United States Patent [19]

Reynolds

[11] 4,291,059

[45] Sep. 22, 1981

[54] CYCLOALIPHATIC COMPOUNDS, ANALGESIC COMPOSITIONS THEREOF AND METHOD OF USE THEREOF AS ANALGESICS

[75] Inventor: Derek P. Reynolds, Hertfordshire, England

[73] Assignee: Glaxo Group Limited, England

[21] Appl. No.: 86,333

[22] Filed: Oct. 19, 1979

[30] Foreign Application Priority Data

Oct. 25, 1978 [GB] United Kingdom ............... 41871/78
Oct. 25, 1978 [GB] United Kingdom ............... 41873/78

[51] Int. Cl.³ ............. A61K 31/55; A61K 31/40; C07D 295/10
[52] U.S. Cl. ............................. 424/311; 424/244; 424/267; 424/274; 424/305; 424/308; 260/239 BF; 260/326.4; 260/326.43; 560/107; 560/221; 560/250; 546/239; 564/307; 260/239 A
[58] Field of Search ............ 260/570.5 CA, 326.4, 260/326.43, 239 B, 239 BF, 239 AR; 560/107, 221, 250; 546/239; 424/244, 267, 274, 308, 305, 311

[56] References Cited

PUBLICATIONS

Bordwell et al., "J. Org. Chem.", vol. 28, pp. 1765–1769 (1963).
Flick et al., "Arzneim-Forsch", vol. 28 (1) (1a), pp. 107–113 (1978).

*Primary Examiner*—Robert T. Bond
*Attorney, Agent, or Firm*—Bacon & Thomas

[57] ABSTRACT

Compounds are disclosed of general formula (I)

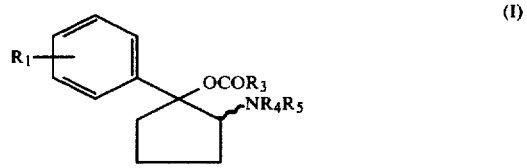

(I)

in which $R_1$ represents a hydrogen atom, a halogen atom or a group $OR_2$, in which $R_2$ represents a hydrogen atom, an alkyl group or an acyl group, $R_3$ represents hydrogen or an alkyl, alkenyl or aryl group, $R_4$ and $R_5$ which may be the same or different, each represents a hydrogen atom or an alkyl, alkenyl or alkynyl group optionally substituted by an aryl or cycloalkyl group;

or $R_4$ and $R_5$ together with the nitrogen atom may form a saturated four to seven membered ring, with the provisos that, when $R_4$ and $R_5$ simultaneously represent hydrogen atoms then (i) when $R_1$ is hydrogen then $R_3$ is not methyl and (ii) the compounds are the $\beta$-isomers;

and their physiologically acceptable salts.

Compounds of formula (I) may be prepared from the corresponding $\alpha$- or $\beta$-configuration alcohols, from an aziridine intermediate or by a variety of alkylation procedures whereby the group $R_4$ and/or $R_5$ is introduced. The compounds (I) and their salts have analgesic activity and may be formulated as pharmaceutical compositions in conventional manner.

19 Claims, No Drawings

CYCLOALIPHATIC COMPOUNDS, ANALGESIC COMPOSITIONS THEREOF AND METHOD OF USE THEREOF AS ANALGESICS

This invention relates to cycloaliphatic compounds, to processes for the production thereof and to pharmaceutical compositions containing them.

We have found that certain cyclopentylamine compounds have analgesic activity.

According to the invention there are provided compounds of the general formula (I):

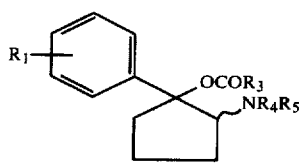

in which
$R_1$ represents a hydrogen atom, a halogen atom or a group $OR_2$, in which $R_2$ represents a hydrogen atom, an alkyl group or an acyl group;
$R_3$ represents a hydrogen atom or an alkyl, alkenyl or aryl group;
$R_4$ and $R_5$, which may be the same or different, each represents a hydrogen atom or an alkyl, alkenyl or alkynyl group optionally substituted by an aryl or cycloalkyl group; or
$R_4$ and $R_5$ together with the nitrogen atom to which they are attached form a saturated four to seven membered ring;
with the proviso that, when $R_1$, $R_4$ and $R_5$ simultaneously represent hydrogen atoms $R_3$ does not represent a methyl group;
and physiologically acceptable salts thereof.

The term alkyl is intended to cover straight chain or branched chain alkyl groups having 1 to 6 carbon atoms, preferably 1 to 4 carbon atoms.

The term cycloalkyl is intended to cover cycloalkyl groups having from 3 to 6 carbon atoms, for example, cyclopropyl.

The term alkenyl is intended to cover straight chain or branched chain alkenyl groups having 3 to 6 carbon atoms.

The term alkynyl is intended to cover straight chain or branched chain alkynyl groups having 3 to 6 carbon atoms, e.g. propynyl.

The term aryl is intended to cover monocarbocyclic and monoheterocyclic aryl groups and is preferably phenyl.

The term acyl is intended to cover aliphatic or aromatic acyl groups, preferably alkanoyl groups having one to six carbon atoms, alkenoyl groups having three to six carbon atoms and aroyl groups, preferably benzoyl.

As examples of physiologically acceptable salts, there may be mentioned in particular physiologically acceptable acid addition salts. Particularly useful salts are those with mineral acids such as hydrochloric and sulphuric acids and with organic acids such as maleic, fumaric and acetic acids.

The invention also extends to all possible diastereoisomers and optical enantioners of compounds of general formula (I) with the proviso that, when $R_4$ and $R_5$ simultaneously represent hydrogen atoms, the compounds of general formula (I) are the β-isomers. Diastereoisomers wherein the group $-NR_4R_5$ is cis to the phenyl ring are designated herein as β-isomers and compounds wherein the configuration of the groups is trans are designated as α-isomers.

Preferred compounds are those in which $R_1$ represents a hydrogen atom, a halogen atom, for example chlorine or fluorine, or an alkoxy group most preferably methoxy. In general the group represented by $R_1$ is preferably in the m-position in the phenyl ring.

It is also preferred for $R_3$ to represent an alkyl group, most preferably methyl or ethyl.

Other preferred compounds are those in which $R_4$ represents a hydrogen atom or an alkyl group most preferably methyl or ethyl and those in which $R_5$ is a hydrogen atom or an alkyl group, most preferably methyl, ethyl or propyl or an alkylcycloalkyl group, most preferably cyclopropylmethyl, or an alkenyl group, most preferably allyl. Other preferred compounds are those wherein $R_4$ and $R_5$ together with the nitrogen atom represent a saturated 5- or 6-membered ring.

Particularly preferred compounds according to the invention are those wherein $R_1$ is a methoxy group substituted in the m-position of the phenyl ring or, most preferably, a hydrogen atom; $R_3$ is an alkyl group, particularly methyl or ethyl; and $R_4$ is hydrogen or an alkyl group, particularly methyl; and $R_5$ is an alkyl group, particularly methyl or ethyl. A further preferred class of compounds is than wherein $R_4$ and $R_5$ are both hydrogen atoms and $R_3$ is an ethyl group. A particularly preferred class of compounds is that wherein $R_4$ is a hydrogen atom or a methyl group and $R_5$ is a methyl group.

The preferred compounds are the β-isomers.

Preferred specific compounds according to the invention are 2β-dimethylamino-1-phenylcyclopentanol propanoate ester; 2β-dimethylamino-1-phenylcyclopentanol acetate ester; 2β-methylamino-1-phenylcyclopentanol propanoate ester; and their physiologically acceptable acid addition salts.

Another compound of particular interest is the propanoate ester of 2β-amino-1-phenylcyclopentanol, preferably as the hydrochloride or maleate.

A particularly preferred compound is 2β-methylamino-1-phenylcyclopentanol, propanoate ester, hydrogen sulphate or hydrogen maleate.

Compounds falling within the general formula (I) have been shown to have analgesic activity using standard pharmacological tests. These methods include (1) measurement of the suppression in abdominal constriction response caused by acetylcholine in the mouse (Collier H. O. J. et al Br. J. Pharmac. 32, 295–310 (1968)); (2) inhibition of pain in the mouse induced by the hot plate method (Woolfe G. and Macdonald A. D., J. Pharmac. Exp. Ther. 80 300–307 (1944)); (3) reduction of the pain response to electrical stimulation of the dental pulp in the dog (Marriot A. S. et al, Brit. J. Pharmac. 55 314p (1975)); and (4) reduction of pain in the rat paw pressure test (Randall L. O. and Selitto J. J., Arch. Int. Pharmacodyn. Ther. 11 409 (1957)).

The compounds of general formula (I) and their salts can therefore be considered for use in the relief of pain e.g. toothache, headache, muscle pains, arthritis, dysmenorrhea and neuralgia etc.

The compounds according to the invention may be formulated for administration as the free base or as a non-toxic physiologically acceptable salt, in any convenient way and the invention includes within its scope pharmaceutical compositions containing at least one compound according to the invention adapted for use in human or veterinary medicine. Such compositions may be formulated in conventional manner using one or more pharmaceutically acceptable carriers or excipients and, if desired, supplementary medicinal agents.

Other active compounds which may be incorporated include other analgesic, antiinflammatory or antipyretic compounds e.g. aspirin or paracetamol.

Thus the compounds according to the invention may be formulated for oral, buccal, topical, parenteral or rectal administration. Oral administration is preferred.

For oral administration, the pharmaceutical composition may take the form of, for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration. Formulations for injections may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

The daily dosage of the compounds may vary between 10 mg and 2 g, for example 200 mg to 1 g. The dosage units may be formulated to give the whole or part of the daily dosage in a single unit. Oral administration is preferred, preferably in two to four daily doses.

The invention also provides a method of treatment for the relief of pain which comprises administering to a patient an effective amount of a compound according to the invention.

The compounds of general formula (I) in which $R_4$ and $R_5$ have the meanings given other than hydrogen, may be prepared by acylating the corresponding alcohol of general formula (II):

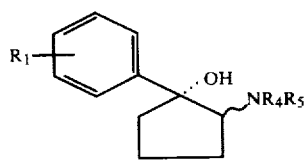
(II)

Suitable acylating agents include formate esters, acid halides, for example acetyl chloride and propionyl chloride, and anhydrides (including mixed anhydrides) for example acetic anhydride.

The reaction of the alcohol of general formula (II) with an acid halide may, optionally, be carried out with heating, for example, at a temperature up to 100° C. The reaction may be carried out either in the absence or presence of a solvent such as dimethylformamide, tetrahydrofuran or acetonitrile and optionally in the presence of an inorganic base such as potassium carbonate or bicarbonate or an organic base such as pyridine or triethylamine.

The reaction of the alcohol of general formula (II) with an acid anhydride is preferably carried out with heating and optionally in the presence of a base such as triethylamine either in the absence or presence of 4-dimethylaminopyridine.

The corresponding alcohol having the β-configuration i.e. of general formula (III):

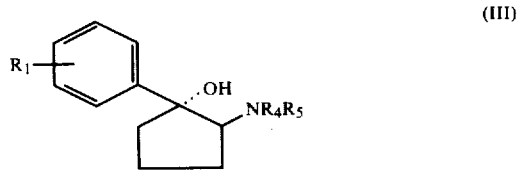

wherein $R_4$ and $R_5$ have the meanings given for general formula (I)
may be prepared from an olefin of general formula (IV):

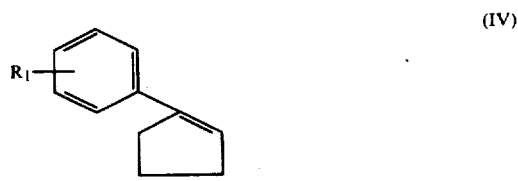

using an appropriate peracid, e.g. peracetic acid, preferably buffered with sodium acetate with the resulting epoxide of general formula (V):

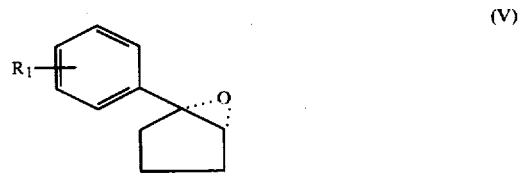

being then heated with aqueous ammonia or with a primary or secondary amine to give a mixture of the alcohol or general formula (III) and an isomer thereof from which the desired alcohol (III) can readily be separated.

Alcohols having the α-configuration i.e. of formula (VI):

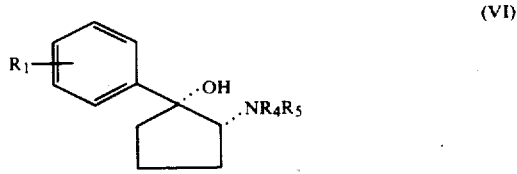

wherein $R_4$ and $R_5$ have the meanings given and are other than hydrogen atoms
may be prepared either by the reaction of a Grignard reagent, e.g. phenyl magnesium bromide, or an aryl lithium, e.g. phenyl lithium, with a ketone of general formula (VII):

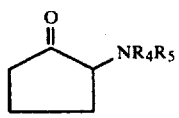

(VII)

wherein $R_4$ and $R_5$ are as defined for compounds (VI).

An alternative method to compounds of the invention having the β-configuration involves reacting an aziridine of general formula (VIII):

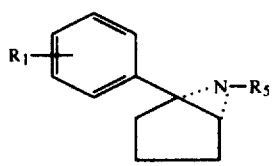

(VIII)

where $R_1$ and $R_5$ are as defined for formula (I) with an organic acid $R_3COOH$ e.g. propionic acid, optionally in a solvent such as toluene and preferably with heating, for example to a temperature of 50°–100° C.

When $R_5$ represents a hydrogen atom then the aziridine (VIII) may be prepared from an olefin of general formula (IX):

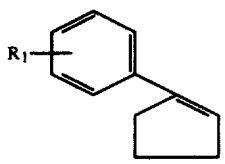

(IX)

by treatment with iodine isocyanate.

The resulting compound of general formula (X):

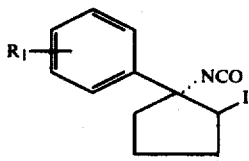

(X)

may then be hydrolysed with a suitable acid e.g. concentrated hydrochloric acid in a solvent such as acetone to give the iodoamine salt of the general formula (XI):

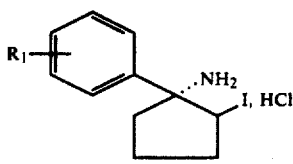

(XI)

which may then be neutralized with a suitable base e.g. sodium hydroxide to give the aziridine (VIII) where $R_5$ represents a hydrogen atom.

When, however, as preferred, $R_5$ is other than a hydrogen atom then the aziridine of general formula (VIII) may be prepared from an alcohol of general formula (III) where $R_4$ is hydrogen by treatment with a halogenating agent such as thionyl chloride. The resulting chloroamine hydrochloride of general formula (XII):

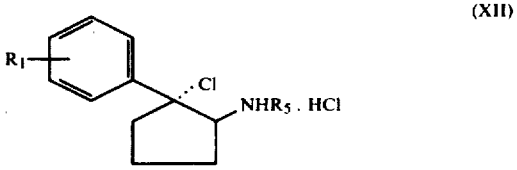

(XII)

may be treated, if desired, with a suitable base e.g. sodium hydroxide, to give the aziridine of general formula (VIII).

Another process for the preparation of aziridines of formula (VIII) wherein $R_5$ is other than a hydrogen atom involves reacting an amino alcohol of formula (XIII):

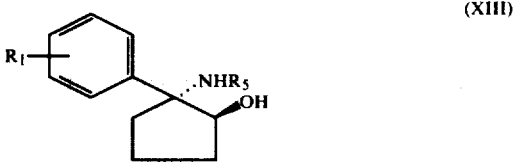

(XIII)

with concentrated sulphuric acid. The resulting compound of formula (XIV) may then be neutralised with a suitable base, e.g. sodium

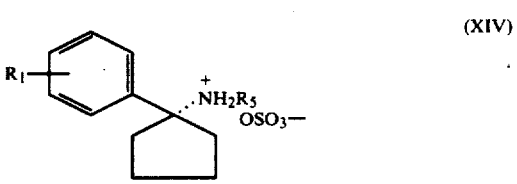

(XIV)

hydroxide to give the aziridine of formula (VIII).

The amino alcohol (XIII) may be obtained by separation from a mixture thereof with the alcohol (III) which is obtained by reaction of an epoxide (V) with aqueous ammonia or with a primary or secondary amine as previously described.

Alcohols of general formula (II) wherein $R_4$ is other than hydrogen may be prepared from compounds in which $R_4$ is a hydrogen atom by acylation using an activated derivative of a carboxylic acid, e.g. an acid halide or acid anhydride, to give a compound of general formula (XV):

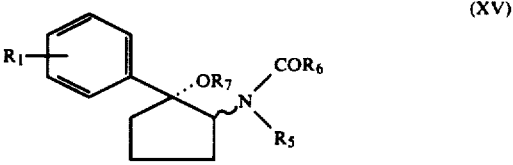

(XV)

wherein $R_6$ is the residue of the group $R_4$ and $R_7$ is a hydrogen atom or the group $COR_6$.

Reduction of this amide with, for example, lithium aluminium hydride gives a compound of general formula (II) in which $R_4$ corresponds to the group $CH_2R_6$.

The group $R_5$ (where $R_5$ is other than a hydrogen atom) may be introduced into an alcohol of the formula (XVI):

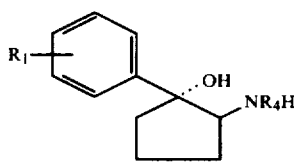
(XVI)

or the formula (XVII):

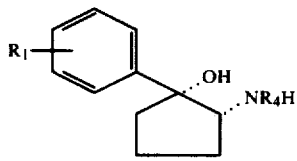
(XVII)

wherein $R_1$ and $R_4$ are as previously defined by a standard alkylating procedure, for example using an alkyl or allyl halide.

Alternatively, standard alkylating procedures may be used to prepare β-isomers of the general formula (I) by introducing the group $R_4$ and/or $R_5$ into corresponding β-isomers wherein $R_4$ and/or $R_5$ is hydrogen.

Thus, β-isomers of general formula (I) wherein $R_4$ is a hydrogen atom may be prepared by monoalkylation of the primary amine of general formula (XVIII):

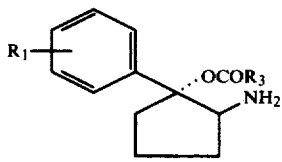
(XVIII)

wherein $R_1$ represents a hydrogen atom, a halogen atom or a group $OR_2$ (where $R_2$ is as previously defined) and
$R_3$ represents a hydrogen atom or an alkyl, alkenyl or aryl group.

The alkylation may be effected with a compound of formula $R_5X$ where X is a leaving group such as a halide, acetate, tosylate or alkyl sulphate ($R_5SO_4$).

Alternatively, the group $R_5$ may be introduced into the amine (XVIII) by reaction with an appropriate aldehyde or ketone. This reaction may be carried out in the presence of a reducing agent such as hydrogen and a noble metal catalyst, e.g. platinum, or the aldehyde or ketone may first be condensed with the primary amine (XVIII) and the resulting product hydrogenated in the presence of a noble metal catalyst, e.g., platinum.

According to a further possible alkylation reaction, a primary amine of formula (XVIII) may be converted directly into the corresponding dialkylderivatives in which $R_4$ and $R_5$ are the same and other than hydrogen atoms. For example, the primary amine (XVIII) may be reacted with an excess of an alkylating agent of formula $R_5X$ (where X is a leaving group as previously defined) or with an excess of an aldehyde or ketone in the presence of hydrogen and a suitable metal catalyst.

Alternatively, a reductive alkylation procedure may be used to prepare tertiary amines of general formula (I). In this process, a secondary amine of formula (XIX):

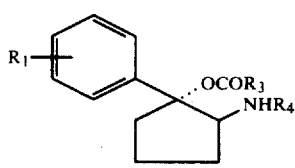
(XIX)

wherein $R_1$, $R_3$ and $R_4$ are as defined in claim 1 and $R_4$ is other than a hydrogen atom
is treated with an appropriate aldehyde or ketone under reducing conditions e.g. hydrogen and a noble metal catalyst.

The olefinic starting materials of general formula (IV) previously defined may be prepared from cyclopentanone by a Grignard reaction using the appropriate aryl magnesium halide or by reaction with an appropriate aryl lithium. Dehydration of the product with, for example, sulphuric acid and acetic acid, yields a compound of general formula (IV).

The ketonic starting materials of general formula (VII) may be prepared from cyclopentene using the method described above for converting olefins of general formula (IV) into amino alcohols of general formula (III) i.e. using a peracid and an amine. The resulting amino alcohol of formula (XX):

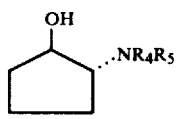
(XX)

may then be oxidised using a suitable oxidising agent such as chromium trioxide, to give a ketone (VII).

The following Example is given of pharmaceutical compositions using a compound according to the invention as active ingredient.

EXAMPLE OF PHARMACEUTICAL COMPOSITIONS

Tablets (a) Direct compression formulae

| Constituents | mg/tablet | |
|---|---|---|
| Active ingredient | 10 mg | 50 mg |
| Microcrystalline cellulose | 109.5 mg | 149 mg |
| Magnesium Stearate | 0.5 mg | 1 mg |

The powders are mixed together and compressed directly, using 6.5 mm diameter punches to produce tablets weighing about 120 mg for the smaller tablets and 9 mm diameter punches to produce the larger tablets weighing about 200 mg. Tablets of other strengths may be prepared similarly as required.

(b) Wet granulation formulae

| | mg/tablet | |
|---|---|---|
| Active ingredient | 10.0 | 50.0 |
| Lactose | 89.4 | 122.0 |
| Maize Starch | 14.0 | 19.0 |
| Pregelatinised Maize Starch | 6.0 | 8.0 |
| Magnesium Stearate | 0.5 | 1.0 |

The powders are mixed, moistened with distilled water, made into granules, and dried using standard techniques.

The dried granules are compressed into tablets as described for the direct compression formulae.

Capsules

Active ingredient (10 mg) is mixed with about 110 mg of microcrystalline cellulose BPC and filled into No. 3 hard gelatin capsules using standard techniques. Other doses of active ingredient may be prepared by adjusting the amount of microcrystalline cellulose used and/or different size capsules.

Injection

Sufficient active ingredient is dissolved in Water for Injections to make a 10 mg/ml solution, and sodium chloride is added to adjust the tonicity of the solution if necessary.

The solution is filled into suitably sized ampoules (1, 5 or 10 ml) sealed by fusion of the glass and sterilised by heating in an autoclave according to standard practice. The solution may also be sterilised by filtration and filled into sterile ampoules under aseptic conditions using standard techniques.

The following Examples illustrate compounds and their method of production according to the invention. The production of starting materials for use in these Examples is described first under the heading Preparations 1-14.

PREPARATION 1

2β-Methylamino-1-phenylcyclopentanol

A solution of 1-phenyl-6-oxabicyclo [3.1.0] hexane (1 g) in ethanolic methylamine (33%; 10 ml) was heated for 24 hours at 140° in an autoclave. The solvent was removed in vacuo and the residue partitioned between 2 M hydrochloric acid and ether. The aqueous phase was separated, basified with 5 M sodium hydroxide solution and extracted with ether. The extract was dried and evaporated to leave an off-white solid (0.9 g) which was crystallised from benzene to give the title compound as colourless rods (0.5 g) m.p. 123°–124°.

PREPARATION 2

2β-Dimethylamino-1-phenylcyclopentanol

Method A

A solution of 2β-methylamino-1-phenylcyclopentanol (1.0 g) in formic acid (98%; 3 ml) and formaldehyde (36%; 3 ml) was heated at 100° until evolution of carbon dioxide ceased (1 hour). The solution was poured into 5 M sodium hydroxide solution (10 ml) and extracted with ether (2×25 ml). The extracts were dried and evaporated to give the title compound as a colourless liquid (1.0 g).

2β-Dimethylamino-1-phenylcyclopentanol was dissolved in ether and treated with ethereal hydrogen chloride. The hydrochloride that precipitated was filtered off and recrystallised from a mixture of methanol and ethyl acetate as colourless micro-crystals, m.p. 133°–134°.

Method B

A solution of 1-phenyl-6-oxabicyclo[3.1.0.]hexane (20 g) in ethanolic dimethylamine (33%; 100 ml) was heated for 20 hours in an autoclave at 140°. The solvent was removed in vacuo and the residue dissolved in ether (200 ml). The ethereal solution was extracted with 2 M hydrochloric acid (3×50 ml) and the acid extracts were neutralized with sodium carbonate. The mixture was extracted with ether (3×50 ml) and the combined extracts dried and evaporated. The residue was distilled in vacuo to give a mixture of 2β-dimethylamino-1-phenylcyclopentanol and 2β-dimethylamino-2-phenylcyclopentanol as a pale yellow oil (23.7 g) b.p. 92°–94° (0.4 mm). To a stirred solution of the oil (23.7 g) in dry dimethylformamide (15 ml) was added a solution of anhydrous hydrogen chloride (4.2 g) in dry dimethylformamide (20 ml). The temperature rose to 45° and a colourless solid slowly separated out. The mixture was cooled to 10° and the colourless crystals of 2β-dimethylamino-2-phenylcyclopentanol hydrochloride (9.2 g) were filtered off. The filtrate was poured onto ice, basified with 5 M sodium hydroxide solution and extracted with ether (2×100 ml) and then light petroleum ether (b.p. 40°–60°) (100 ml). The combined organic extracts were washed with water (3×50 ml), dried and evaporated to leave a brown oil (13 g) which was distilled in vacuo to give 2β-dimethylamino-1-phenylcyclopentanol as a light yellow liquid (10 g) b.p. 90° (0.2 mm).

Method C

Methyl iodide (0.8 g) was added dropwise to a solution of 2β-methylamino-1-phenylcyclopentanol (1.0 g) in tetrahydrofuran (10 ml) at room temperature. After 2 hours the solution was concentrated in vacuo, basified with 5 M sodium hydroxide solution and extracted with ether (2×25 ml). The extracts were dried and evaporated and the residue distilled in vacuo to give a pale yellow liquid (0.3 g) b.p. 90° (0.2 mm).

PREPARATION 3

2α-Dimethylamino-β 1-phenylcyclopentanol, fumarate

Jones reagent (60 ml) [from chromium trioxide (14 g) in water (100 ml) and concentrated sulphuric acid (12 ml)] was added dropwise to a cooled, stirred solution of 2β-dimethylaminocyclopentanol (12.8 g) in water (10 ml). The solution was stirred at room temperature for 1 hour, poured into sodium bicarbonate solution and extracted with chloroform. The extracts were dried and evaporated to give 2-dimethylaminocyclopentanone as a pale yellow oil. The oil was immediately dissolved in dry ether (10 ml) and added dropwise to a freshly prepared solution of phenyl magnesium bromide [from magnesium (5 g) and bromobenzene (31 g)] in ether (90 ml). The solution was stirred for 15 hours, saturated ammonium chloride solution was added and the resulting mixture was extracted with ether. The extracts were dried and evaporated to leave a pale yellow oil which was partitioned between ether (50 ml) and 2 M hydrochloric acid (50 ml). The aqueous phase was separated, basified and extracted with ether (2×50 ml). Evaporation of the dried extracts afforded a brown oil which was distilled in vacuo to give 2α-dimethylamino-1-phenylcyclopentanol as a pale yellow oil (2.2 g) b.p. 125°–130° C. (0.1 mm). A portion (0.5 g) was dissolved in ethyl acetate (10 ml) and treated with a solution of fumaric acid (0.3 g) in ethyl acetate (50 ml). The fumarate salt that precipitated was filtered off and crystallised from a mixture of methanol and ethyl acetate to give the title compound as colourless microcrystals (0.52 g) m.p. 145°–147°.

In a similar manner was prepared: 2α-Diethylamino-1-phenylcyclopentanol; pale yellow oil, b.p. 95°–100° (0.1 mm).

PREPARATION 4

2β-Dimethylamino-1-(3-methoxyphenyl)cyclopentanol, hydrochloride

1-(3-Methoxyphenyl)-6-oxabicyclo[3.1.0]hexane

A solution of sodium acetate trihydrate (6 g) in peracetic acid (38 ml) was added dropwise to a stirred solution of 1-(3-methoxyphenyl) cyclopentene (33.5 g) in dichloromethane (200 ml), maintaining the temperature in the range 0°–10°. The solution was stirred for 3 hours at room temperature and then washed with 8% aqueous sodium bicarbonate (700 ml) and 8% sodium thiosulphate solution (400 ml). The organic phase was separated, dried and evaporated and the residue was distilled in vacuo to give the title compound as a colourless oil (25 g) b.p. 89°–92° (0.01 mm).

2β-Dimethylamino-1-(3-methoxyphenyl)cyclopentanol, hydrochloride

A solution of 1-(3-methoxyphenyl)-6-oxabicyclo[3.1.0]hexane (24.2 g) in ethanolic dimethylamine (33%; 73 ml) was heated for 18 hours at 140° in an autoclave. The solvent was removed in vacuo to leave a brown oil which was partitioned between 2 M hydrochloric acid and ether. The aqueous phase was separated, washed with light petroleum ether (b.p. 60°–80°), basified with 2 M sodium hydroxide solution and extracted with ether (2 × 100 ml). The combined organic extracts were dried and evaporated to leave a brown oil (26.8 g). Treatment of a solution of this oil (25.3 g) in dry dimethylformamide (70 ml) with a solution of anhydrous hydrogen chloride (6.61 g) in dimethylformamide (66 ml) resulted in preferential crystallisation of the title compound. It was recrystallised from a mixture of methanol and ethyl acetate as colourless microcrystals (14.2 g) m.p. 185°–186°.

PREPARATION 5

2β-Ethylmethylamino-1-phenylcyclopentanol

N-(2-Hydroxy-2α-phenylcyclopentyl)-N-methylacetamide

A solution of 2β-methylamino-1-phenylcyclopentanol (1 g) in dimethylformamide (10 ml) was treated with triethylamine (1.4 g) and acetic anhydride (0.7 g). The solution was kept at room temperature for 16 hours and then neutralised with 8% sodium bicarbonate solution and extracted with ethyl acetate (2 × 50 ml). The extracts were dried and evaporated to leave a pale yellow solid which was recrystallised from ethyl acetate to give the title compound as colourless rods (1.0 g) m.p. 129.5°–130.5°.

2β-Ethylmethylamino-1-phenylcyclopentanol

A solution of N-(2-hydroxy-2α-phenylcyclopentyl) N-methylacetamide (5 g) in dry tetrahydrofuran (30 ml) was added dropwise to a stirred suspension of lithium aluminium hydride (1 g) in dry tetrahydrofuran (20 ml). The mixture was stirred and refluxed overnight and then decomposed with water. The inorganic salts were filtered off and the filtrate dried and evaporated to leave a red gum which was distilled in vacuo to give the title compound as a light green gum (3 g) b.p. 150° (0.1 mm).

PREPARATION 6

2β-[Methyl(2-propenyl)amino]-1-phenylcyclopentanol

Allyl bromide (0.94 ml) was added dropwise to a solution of 2β-methylamino-1-phenylcyclopentanol (1.9 g) in dry dimethylformamide (15 ml) and the resulting solution was kept at room temperature for 3 days. The solution was poured into water (50 ml), basified with 2 M sodium carbonate solution and extracted with ethyl acetate (3 × 25 ml). The extracts were washed with water (3 × 80 ml), dried and evaporated to give a yellow oil (1.6 g) which was distilled in vacuo to give the title compound as a colourless liquid (1.0 g) b.p. 105° (0.02 mm).

PREPARATION 7

2β-[(Cyclopropylmethyl)methylamino]-1-phenylcyclopentanol

N-(2-Hydroxy-2α-phenylcyclopentyl)-N-methylcyclopropane carboxamide

Cyclopropane carbonyl chloride (4.4 g) was added dropwise and with cooling to a solution of 2β-methylamino-1-phenylcyclopentanol (6.65 g) in dry pyridine (70 ml). The mixture was allowed to attain room temperature. After 3 days the suspension was poured into a mixture of concentrated hydrochloric acid (94.5 ml), water (280 ml) and ice (278 g). The product was extracted into ether (2 × 100 ml) and the extracts were washed with 2 N sodium carbonate solution (2 × 30 ml) and water, dried and evaporated to give the amide as a yellow oil (7.7 g).

2β-[(Cyclopropylmethyl)methylamino]-1-phenylcyclopentanol

A solution of N-(2-hydroxy-2α-phenylcyclopentyl)-N-methylcyclopropane carboxamide (2.6 g) in dry tetrahydrofuran (30 ml) was added dropwise under nitrogen to a stirred suspension of lithium aluminium hydride (0.46 g) in dry tetrahydrofuran (10 ml). The suspension was stirred and refluxed for 6 hours and then decomposed with water. The inorganic salts were filtered off and the filtrate was evaporated. The liquid residue was partitioned between ether (50 ml) and water (50 ml). The organic phase was separated, washed with water (2 × 20 ml), dried and evaporated to give a colourless oil (2.25 g), which was distilled in vacuo to give the title compound as a colourless Oil (2.0 g) b.p. 145° (0.04 mm).

2β-[Methyl(2-phenylethyl)amino]-1-phenylcyclopentanol

A mixture of 2β-methylamino-1-phenylcyclopentanol (6.65 g), anhydrous sodium carbonate (5.25 g) and 2-phenylethylbromide (7.14 g) in butanone (150 ml) was stirred and refluxed for 41 hr. The solid was filtered off and the filtrate evaporated in vacuo to give a liquid which was partitioned between water (100 ml) and ether (100 ml). The organic phase was separated and extracted with 2 N hydrochloric acid (2 × 50 ml). The combined acid extracts were neutralised with sodium bicarbonate solution (8%) and the product was extracted with ether (2 × 50 ml). The combined organic extracts were washed with water (2 × 10 ml), dried and evaporated to give a brown liquid (5.1 g) which was distilled in vacuo to give the title compound (4.7 g) b.p. 205° (0.07 mm).

PREPARATION 9

2β-Methylpropylamino-1-phenylcyclopentanol

Propyl iodide (2.8 g) was added to a solution of 2β-methylamino-1-phenylcyclopentanol (2.85 g) in tetrahydrofuran (30 ml) and refluxed for 45 hr. The solution was evaporated in vacuo and the residue was partitioned between 2 N sodium carbonate solution (25 ml) and ether (50 ml). The organic phase was separated and extracted with 2 M hydrochloric acid (2×20 ml). The combined acid extracts were neutralised with 2 N sodium carbonate solution and the product was extracted with ether (2×30 ml). The combined organic extracts were washed with water (2×10 ml), dried and evaporated to give a yellow oil (1.4 g) which was distilled in vacuo to give the title compound as a pale green liquid (1.09 g) b.p. 110° (0.03 mm).

PREPARATION 10

2β-Methylamino-1-(3-chlorophenyl)cyclopentanol, hydrochloride

A solution of 1-(3-chlorophenyl)-6-oxabicyclo[3.1.0]hexane (35 g) in ethanolic methylamine (33%; 100 ml) containing dichloromethane (10 ml) was heated for 22 hours in an autoclave at 150°. The solvent was removed in vacuo to give a brown oil (41 g) which was triturated with acetone to give a colourless solid (11.8 g). This was recrystallised from a mixture of methanol and ethyl acetate to give the title compound as colourless microcrystals (8.5 g) m.p. 180°-181°.

PREPARATION 11

2β-Dimethylamino-1-(3-chlorophenyl)cyclopentanol, fumarate

A solution of 2β-methylamino-1-(3-chlorophenyl)cyclopentanol (11.5 g) in formic acid (36 ml) and formaldehyde (34 ml) was heated for 21 hours at 100°. The solution was cooled to room temperature and then poured into ice-cold 5 M sodium hydroxide solution (200 ml) and extracted with ether (2×300 ml). The extracts were dried and evaporated to give a pale yellow oil (9.2 g) which was redissolved in ether (50 ml) and added to a hot solution of fumaric acid (4.5 g) in ethyl acetate (150 ml). The solution was cooled to give a colourless solid which was filtered off and recrystallised from a mixture of methanol and ethyl acetate to give the title compound as colourless microcrystals (12.5 g), m.p. 180°-182°.

PREPARATION 12

1-Phenyl-2β-pyrrolidinylcyclopentanol, fumarate

A solution of 1-phenyl-6-oxabicyclo[3.1.0]hexane (9 g) and pyrrolidine (6 ml) in ethanol (10 ml) was heated in an autoclave for 7 hours at 130°. The solvent was removed in vacuo to give a brown oil which was partitioned between ether and 2 M hydrochloric acid. The aqueous layer was separated, basified and extracted with ether. Evaporation of the dried extracts afforded a mixture of the title compound and 2-phenyl-2β-pyrrolidinylcyclopentanol as a brown oil (6.0 g). The mixture was absorbed onto a silica column (40 g) and eluted with a mixture of methanol and ethyl acetate (1:1) to give 2-phenyl-2β-pyrrolidinylcyclopentanol. Continued elution afforded a brown oil which was distilled in vacuo to give 1-phenyl-2β-pyrrolidinylcyclopentanol as a pale yellow oil (290 mg) b.p. 115°-120° (0.1 mm). A solution of the base in ethyl acetate (5 ml) was added to a solution of fumaric acid (150 mg) in ethyl acetate (10 ml). The precipitate that formed was filtered off and recrystallised from a mixture of methanol and ethyl acetate to give the title compound as colourless microcrystals (363 mg) m.p. 187°-189°.

PREPARATION 13

2β-Methylamino-2-phenylcyclopentanol

A solution of 1-phenyl-6-oxabicyclo[3.1.0]hexane (20 g) and 33% ethanolic methylamine (60 ml) was heated at 155° for 20 hours. The solvent was removed in vacuo to leave a dark tan liquid which crystallised on cooling. Trituration with light petroleum ether (b.p. 40°-60°) afforded 2β-methylamino-1-phenylcyclopentanol as colourless crystals (12 g). The filtrate was concentrated to give grey crystals (7 g) which were recrystallised three times from ethyl acetate to give the title compound as colourless needles (1.0 g) m.p. 89°-90°.

PREPARATION 14

2β-Iodo-1-phenylcyclopentanamine, hydrochloride

1-Phenylcyclopentene (30.25 g) and silver cyanate (45 g) in methylene chloride (500 ml) were stirred under nitrogen with ice cooling. Iodine (53.5 g, 0.21 mole) was added and the resulting mixture was stirred in the ice bath for a further 4 hr.

The silver salts were filtered off on Hyflo and the filtrate was washed with aqueous sodium sulphite (ca. 5%; 200 ml). The solution was dried (MgSO$_4$) and evaporated in vacuo to give a light brown oil (60 g).

The oil was dissolved in acetone (400 ml), the solution stirred with ice cooling and concentrated hydrochloric acid (100 ml) was slowly added. The ice bath was removed after 20 mins and the resulting mixture was stirred at room temperature for 7 hr. The resulting precipitate was filtered off and washed with acetone to give the title compound as white crystals (23 g) m.p. 140°-2° (dec.).

1-Phenyl-6-azabicyclo[3.1.0]hexane

The iodoamine hydrochloride (10 g), 2 M aqueous sodium hydroxide (50 ml) and ether (50 ml) were stirred with ice cooling for 15 mins and then at room temperature for a further 15 mins. The aqueous layer was washed with ether (100 ml) and the combined ethereal solution washed with saturated brine, dried over sodium sulphate and evaporated in vacuo to give the title compound as a very pale yellow oil (5.1 g).

EXAMPLE 1

2β-Dimethylamino-1-phenylcyclopentanol, propanoate ester, hydrochloride, hemihydrate A solution of propionyl chloride (5 ml) in dry dimethylformamide (15 ml) was added dropwise to a stirred solution of 2β-dimethylamino-1-phenylcyclopentanol (Preparation 2) (10 g) in dry dimethylformamide (35 ml) at 0°. The solution was kept at room temperature overnight, poured onto ice, basified with 5 M sodium hydroxide solution and extracted once with ether (50 ml), and once with light petroleum ether (b.p. 40°-60°) (50 ml). The combined extracts were washed with water (4×50 ml), dried and evaporated to leave a brown liquid which was distilled in vacuo to give the ester as a colourless liquid (8.3 g) b.p. 97° (0.1 mm). A hot solution of 2β-dimethylamino-1-phenylcyclopentanol, propanoate ester (8.3 g) in ethyl acetate (25 ml) was treated first with a solution of anhydrous hydrogen chloride (1.16 g) in ethyl acetate (25 ml) and then with water (0.6 g), to give the hydrochloride as a waxy crystalline solid. The supernatant liquid was decanted off and the residue triturated with ethyl acetate (3×70 ml). The resulting solid was filtered off and recrystallised from ethyl acetate to give 2β-dimethylamino-1-phenycyclopentanol, propanoate ester, hydrochloride, hemihydrate as colourless prisms (5.5 g) m.p. 142°–143°.

EXAMPLE 2

2β-Dimethylamino-1-phenylcyclopentanol, acetate ester, hydrochloride, hemihydrate A solution of 2β-dimethylamino-1-phenylcyclopentanol (Preparation 2) (2.5 g) (contaminated with 2β-dimethylamino-2-phenylcyclopentanol) in acetyl chloride (25 ml) was left at room temperature for 2 hours. The solvent was evaporated and water (25 ml) was added to the residue. The solution was neutralised (sodium carbonate) and the mixture was extracted with ether (3×25 ml). The extracts were dried and evaporated to give a brown oil (2.9 g), which showed two spots, Rf 0.35 and 0.51, by thin layer chromatography (silica, ethyl acetate). The mixture of esters was absorbed onto a silica gel column (120 g) and eluted with a mixture of ethyl acetate and cyclohexane (1:1) to give the slower running 2β-dimethylamino-1-phenycyclopentanol, acetate ester as a colourless oil (1.8 g). It was dissolved in ether and treated with ethereal hydrogen chloride. 2β-Dimethylamino-1-phenylcyclopentanol, acetate ester, hydrochloride, hemihydrate precipitated and was filtered off and crystallised from a mixture of ethanol and ethyl acetate as colourless prisms (1.0 g) m.p. 159°–159.5° (dec.).

EXAMPLE 3

2α-Dimethylamino-1-phenylcyclopentanol, propanoate ester

Propionyl chloride (0.5 g) was added dropwise to a stirred solution of 2α-dimethylamino-1-phenylcyclopentanol (Preparation 3) (1.0 g) in dimethylformamide (15 ml). The solution was stirred for 2 hr. and then poured into saturated sodium bicarbonate solution (50 ml) and extracted with ethyl acetate. The extracts were washed with saturated sodium chloride solutions, dried and evaporated to leave a yellow oil which was distilled in vacuo to give the title compound as a pale yellow oil (1.01 g) b.p. 135° (0.04 mm).

The following compounds were prepared in a similar manner:

2β-Dimethylamino-1-(3-methoxyphenyl)cyclopentanol, acetate ester; colourless liquid b.p. 120° (0.1 mm) from 2β-dimethylamino-1-(3-methoxyphenyl)cyclopentanol (Preparation 4).

2β-Dimethylamino-1-(3-methoxyphenyl)cyclopentanol, propanoate ester; colourless liquid b.p. 140° (0.05 mm) from 2β-dimethylamino-1-(3-methoxyphenyl)cyclopentanol (Preparation 4).

EXAMPLE 4

2β-Ethylmethylamino-1-phenylcyclopentanol, propanoate ester

A solution of propionyl chloride (0.7 ml) in tetrahydrofuran (10 ml) was added dropwise to a stirred mixture of 2β-ethylmethylamino-1-phenylcyclopentanol (Preparation 5) (1.2 g) and potassium carbonate (0.7 g) in refluxing tetrahydrofuran (30 ml). The mixture was refluxed for 3 days and then partitioned between ether and sodium hydroxide solution. The aqueous phase was extracted with ether (25 ml) and the combined organic phases dried and evaporated to leave a yellow oil (1.0 g) which was absorbed onto an alumina column (60 g). Elution with a mixture of ether and light petroleum ether (b.p. 40°–60°), (1:3) afforded a yellow oil which was distilled in vacuo to give 2β-ethylmethylamino-1-phenylcyclopentanol, propanoate ester as a light yellow liquid (0.28 g) b.p. 150° (0.04 mm).

The following compounds were prepared in a similar manner:

2β-Dimethylamino-1-(3-chlorophenyl)cyclopentanol, acetate ester; pale yellow oil, $n_D^{24}$ 1.5303 from 2β-dimethylamino-1-(3-chlorophenyl) cyclopentanol (Preparation 11).

2β-Dimethylamino-1-(3-chlorophenyl)cyclopentanol propanoate ester; brown oil, $n_D^{24}$ 1.5254 from 2β-dimethylamino-1-(3-chlorophenyl)cyclopentanol (Preparation 11).

EXAMPLE 5

2α-Dimethylamino-1-phenylcyclopentanol, acetate ester, fumarate

A solution of 2α-dimethylamino-1-phenylcyclopentanol fumarate (Preparation 3) (4 g), acetic anhydride (2 ml) and 4-dimethylaminopyridine (5 mg) in triethylamine (10 ml) was heated under reflux for 64 hours. The black solution was partitioned between ice-cold 5 M sodium hydroxide solution (25 ml) and chloroform (50 ml). The organic phase was dried and evaporated to give a black oil (3.5 g) which was distilled in vacuo to yield the acetate ester as an orange oil (2.5 g) b.p. 108°–110° (0.2 mm). The oil was dissolved in hot ethyl acetate (25 ml) and a hot solution of fumaric acid (1.3 g) in ethyl acetate (100 ml) was added. The fumarate salt that crystallised out on cooling was filtered off and recrystallised from ethyl acetate to give 2α-dimethylamino-1-phenylcyclopentanol, acetate ester, fumarate as colourless microcrystals (1.7 g) m.p. 178°–180°.

In a similar manner was prepared:

2α-Diethylamino-1-phenylcyclopentanol, propanoate ester; yellow oil b.p. 116°–118° (0.1 mm) from 2α-Diethylamino-1-phenylcyclopentanol (Preparation 3).

EXAMPLE 6

2β-[(Cyclopropylmethyl)methylamino]-1-phenylcyclopentanol, propanoate ester

Dry triethylamine (8.27 ml) was added dropwise over 3 hr to a stirred solution of 2β-[(cyclopropylmethyl)methylamino]-1-phenylcyclopentanol (Preparation 7) (4.9 g) and propionyl chloride (4.17 ml) in dry acetonitrile (60 ml), at room temperature. The mixture was stirred for an additional 2 hr and the solvent was evaporated in vacuo at room temperature. The residue was partitioned between water (50 ml) and ether (50 ml). The aqueous layer was separated and extracted with ether (30 ml) and the combined ether solutions were washed with water (30 ml). The ether solution was extracted with 2 M hydrochloric acid (3×20 ml) and the acid extracts were neutralised with sodium bicarbonate solution (8%) and the product was extracted with ether (2×60 ml). The combined extracts were washed with water (2×20 ml), dried and evaporated to give a brown liquid residue (5.0 g).

A sample (2.5 g) was eluted from an alumina column (80 g) using 1:4 ethyl acetate/petrol as solvent to give the title compound as a pale green liquid (2.3 g) $n_D^{23}$ 1.5172.

The following compounds were prepared in a similar manner:

2β-[Methyl(2-propenyl)amino]-1-phenylcyclopentanol propanoate ester; pale yellow liquid $n_D^{24}$ 1.518 from 2β-[methyl(2-propenyl)amino]-1-phenylcyclopentanol (Preparation 6).

2β-[Methyl(2-phenylethyl)amino]-1-phenylcyclopentanol propanoate ester; pale green liquid $n_D^{23}$ 1.5462 from 2β-[methyl(2-phenylethyl)amino]-1-phenylcyclopentanol (Preparation 8).

2β-Methylpropylamino-1-phenylcyclopentanol propanoate ester; pale green liquid $n_D^{23}$ 1.5682 from 2β-methylpropylamino-1-phenylcyclopentanol (Preparation 9).

1-Phenyl-2β-pyrrolidinylcyclopentanol, propanoate ester; yellow oil b.p. 190° (0.1 mm) from 1-phenyl-2β-pyrrolidinylcyclopentanol (Preparation 12).

2α-Diethylamino-1-phenylcyclopentanol, acetic ester; orange oil b.p. 150° (0.1 mm) from 2α-diethylamino-1-phenylcyclopentanol (Preparation 3).

EXAMPLE 7

2β-Methylamino-1-phenylcyclopentanol, acetate ester, maleate

6-Methyl-1-phenyl-6-azabicyclo[3.1.0]hexane

Method A

2β-Methylamino-1-phenylcyclopentanol (5.0 g) was added over 40 min. with stirring and ice cooling to thionyl chloride (15 ml). The resulting mixture was then stirred at 0° for a further 2 hours. Most of the thionyl chloride was evaporated in vacuo and ether (80 ml) was added to the residue. The ether was decanted from the heavy oil which separated and the oil was dissolved in methanol (25 ml) with ice cooling. The mixture was made strongly alkaline with 5 N sodium hydroxide (ca. 30 ml) and then stirred at 0° for 1 hr and at room temperature for a further ½ hour. Water (300 ml) and salt (30 g) were then added to the mixture and the product was extracted with ether (200 ml). The ether was washed with saturated brine (2×100 ml), dried over sodium sulphate and evaporated in vacuo to leave a dark oil (4.3 g), which was chromatographed on silica gel (150 g) with ether to give the aziridine as a brown oil (1.2 g).

Method B

Concentrated sulphuric acid (2 ml) was added to a suspension of 2β-methylamino-2-phenylcyclopentanol hydrochloride (2 g) in acetonitrile (15 ml). The hydrochloride salt gradually dissolved and the solution was kept at room temperature overnight during which time colourless crystals (2 g) separated out. These were filtered off, washed with acetonitrile, methanol and ether and then added to 5 M sodium hydroxide solution (20 ml). The salt dissolved very quickly and the resulting solution was kept at room temperature overnight during which time the aziridine separated out as a colourless oil. The product was extracted with ether and the extracts dried (MgSO₄) and evaporated to leave a colourless liquid (1.15 g). Distillation in vacuo afforded the title compound as a colourless liquid (0.9 g) b.p. 65° (0.04 mm).

2β-Methylamino-1-phenylcyclopentanol, acetate ester, maleate

6-Methyl-1-phenyl-6-azabicyclo[3.1.0]hexane (0.6 g) and acetic acid (3 ml) were heated on the steam bath for 40 minutes. The solution was cooled, diluted with ether (100 ml) and extracted with 0.5 N sulphuric acid (saturated with salt) (2×35 ml). The aqueous extracts were washed with ether (60 ml) and made basic with solid potassium carbonate. The product was extracted with ether (3×50 ml) and the extracts were dried over sodium sulphate and evaporated to give a pale yellow oil. This oil was converted into its maleate salt (0.7 g) with ethereal maleic acid. This material was combined with a further 0.24 g from a similar reaction and the whole was crystallised by the following procedure:

The solid was dissolved by heating with a saturated (cold) solution of maleic acid in ethyl acetate (ca. 65 ml). The solution was filtered, cooled rapidly and diluted with ether (ca. 70 ml), until turbidity appeared, the mixture then being seeded and scratched vigorously. After 10 minutes ether (30 ml) was added and the mixture was kept at 0° overnight to give the title compound as cream crystals (0.65 g) m.p. 166°-6°.

EXAMPLE 8

2β-Methylamino-1-phenylcyclopentanol, propanoate ester, hydrogen sulphate

6-Methyl-1-phenyl-6-azabicyclo[3.1.0]hexane (0.9 g) and propionic acid (8 ml) were heated on the steam bath for 45 minutes. The mixture was cooled, diluted with ether (100 ml) and extracted with 0.5 N sulphuric acid (3×20 ml). The acid extracts were washed with ether (50 ml) and made alkaline with solid potassium carbonate. The mixture was saturated with salt and extracted with ether (3×50 ml). The extracts were dried and evaporated in vacuo and the residue converted into its sulphate salt with ethereal sulphuric acid.

The salt was dissolved in methanol (5 ml), diluted with ethyl acetate to 75 ml, and seeded to give the title compound as white crystals (0.9 g) m.p. 145°-7°.

This material was combined with a further 0.8 g from a similar experiment and recrystallised from cold methanol and ethyl acetate to give the title compound as colourless crystals (1.61 g) m.p. 153°-4°.

EXAMPLE 9

2-β-Methylamino-1-phenylcyclopentanol, propanoate ester, hydrogen maleate

Propionic acid (16.3 g) was added to a solution of 6-methyl-1-phenyl-6-azabicyclo[3.1.0]hexane (12.7 g) in toluene (63.5 ml) and the solution heated on a steam bath for 1.75 hr. The cooled reaction mixture was washed with 2 N sodium carbonate solution (80 ml) and the aqueous phase was back extracted with ethyl acetate (2×40 ml). The organic phases were combined, dried (MgSO₄) and filtered. The filtrate was added to a cold (20° C.) solution of maleic acid (9 g) in ethyl acetate (180 ml) and the solid that formed was filtered off and washed with a mixture of ethyl acetate (15 ml) and diethylether (15 ml), followed by diethyl ether (20 ml). The solid was dried (40° C.) to give the title compound (14.6 g) m.p. 125°-125.5° C.).

Analysis Found: C, 62.6; H, 6.84; N, 3.80 $C_{15}H_{21}NO_4 \cdot C_4H_4O_4$ requires: C, 62.8; H, 6.93; N, 3.85%

EXAMPLE 10

2β-Amino-1-phenylcyclopentanol, propanoate ester, hydrochloride

1-Phenyl-6-azabicyclo[3.1.0]hexane (Preparation 14) (0.6 g) was dissolved in propionic acid (1.0 ml) and the solution kept at room temperature for 30 hr.

The mixture was diluted with ether (35 ml) and ethereal hydrogen chloride (ca 10 ml) was added. The precipitate was filtered off and the filtrate was kept at room temperature for 45 mins, after which time the colourless crystals of 2-phenyl-2-cyclopenten-1-amine hydrochloride were filtered off (0.025 g) m.p. 240°-5°. The filtrate was seeded, kept at 0° overnight and the cream coloured solid filtered off (0.43 g) m.p. 171°-4°.

This material was combined with a further 0.39 g from similar reactions and the whole was crystallised twice from ethyl acetate to give the title compound as white crystals (0.515 g) m.p. 188.5°-189°.

EXAMPLE 11

2β-Amino-1-phenylcyclopentanol, propanoate ester, hydrogen maleate

A solution of 1-phenyl-6-azabicyclo [3.1.0]hexane (2 g) in propionic acid (15 ml) was kept at room temperature for 65 h. The mixture was then partitioned between ether (2×70 ml) and aqueous potassium carbonate (20%; 150 ml). The ether solution was extracted with sulphuric acid (0.5 N; 2×45 ml) and the acidic extract basified with potassium carbonate. The product was extracted into ether (2×70 ml) and the dried ($Na_2SO_4$) extract evaporated to give the crude ester (2.1 g) as a light brown oil. An excess of a saturated solution of maleic acid in ether was added to the crude ester (2 g) in ether (5 ml) and the precipitated maleate was recrystallised from a mixture of methanol and ethyl acetate to give the title compound as white crystals (1.85 g). T.l.c. Silica, Methanol; ethyl acetate (1:4) Rf 0.4

EXAMPLE 12

2β-Dimethylamino-1-phenylcyclopentanol, propanoate ester

A solution of 2β-amino-1-phenylcyclopentanol propanoate ester, hydrogen maleate (0.35 g) (Example 11) and aqueous formaldehyde (38%, 3 ml) in methanol (10 ml) was hydrogenated at room temperature and pressure over palladium oxide on charcoal (10%; prereduced; 0.2 g). The reaction was stopped when hydrogen (80 ml) had been taken up. The catalyst was filtered off, the filtrate concentrated and the residue partitioned between ether (50 ml) and aqueous potassium carbonate (10% 50 ml). Evaporation of the dried ($Na_2SO_4$) organic solution gave the title compound as a yellow oil (0.25 g). On TLC, silica, methanol; ethylacetate (1:4) this product had the same Rf(0.5) as the product of Example I.

I claim:

1. A compound of the formula (I):

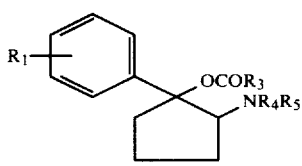

(I)

in which

R₁ represents a hydrogen atom, a halogen atom or a group $OR_2$, in which $R_2$ represents a hydrogen atom, an alkyl group containing 1 to 6 carbon atoms, an alkanoyl group containing 1 to 6 carbon atoms, an alkenoyl group containing 3 to 6 carbon atoms or a benzoyl group;

$R_3$ represents a hydrogen atom or an alkyl containing 1 to 6 carbon atoms, alkenyl containing 3 to 6 carbon atoms or a phenyl group;

$R_4$ and $R_5$, which may be the same or different, each represents a hydrogen atom or an alkyl containing 1 to 6 carbon atoms, alkenyl containing 3 to 6 carbon atoms or alkynyl group containing 3 to 6 carbon atoms optionally substituted by a phenyl or cycloalkyl group containing 3 to 6 carbon atoms; or $R_4$ and $R_5$ together with the nitrogen atom to which they are attached form a saturated four to seven membered ring in which said nitrogen atom is the only heteroatom in said ring; with the provisos that, when $R_4$ and $R_5$ simultaneously represent hydrogen atoms, (i) when $R_1$ represents a hydrogen atom, $R_3$ does not represent a methyl group, and (ii) the compound of formula (I) is the β-isomer, and its physiologically accepted salts.

2. A compound according to claim 1, wherein $R_1$ represents a hydrogen atom, a halogen atom or an alkoxy group containing 1 to 4 carbon atoms.

3. A compound according to claim 1 or 2, wherein $R_3$ represents an alkyl group containing 1 to 6 carbon atoms.

4. A compound according to claims 1 or 2, wherein $R_4$ represents a hydrogen atom or an alkyl group containing 1 to 6 carbon atoms.

5. A compound according to claims 1 or 2, wherein $R_5$ represents an alkyl group containing 1 to 6 carbon atoms, an alkylcycloalkyl group containing 3 to 6 carbon atoms in the cycloalkyl moiety and 1 to 4 carbon atoms in the alkyl moiety or an alkenyl group containing 3 to 6 carbon atoms.

6. A compound according to claims 1 or 2, wherein $R_4$ and $R_5$ together with the nitrogen atom represent a saturated 5- to 6-membered ring in which said nitrogen atom is the only heteroatom in said ring.

7. A compound according to claim 1, wherein $R_1$ represents a hydrogen atom, $R_3$ represents a methyl or ethyl group, $R_4$ represents a hydrogen atom or a methyl group and $R_5$ is a methyl group.

8. A compound according to claim 1, wherein $R_4$ and $R_5$ are both hydrogen atoms and $R_3$ is an ethyl group.

9. 2β-Methylamino-1-phenylcyclopentanol, propanoate ester, hydrogen sulphate or hydrogen maleate.

10. A compound selected from 2β-dimethylamino-1-phenylcyclopentanol propanoate; 2β-dimethylamino-1-phenylcyclopentanol acetate ester; 2β-methylamino-1-phenyl-cyclopentanol propanoate ester; 2β-amino-1-phenylcyclopentanol propanoate and 2,2-dimethyl propanoate ester and their physiologically acceptable acid addition salts.

11. A compound of the formula (I):

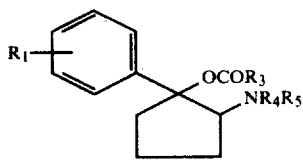

(I)

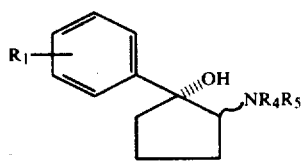

(II)

in which
- $R_1$ represents a hydrogen atom, a halogen atom or a group $OR_2$, in which $R_2$ represents a hydrogen atom, an alkyl group containing 1 to 6 carbon atoms, an alkanoyl group containing 1 to 6 carbon atoms, an alkenoyl group containing 3 to 6 carbon atoms or a benzyl group;
- $R_3$ represents a hydrogen atom or an alkyl containing 1 to 6 carbon atoms, alkenyl containing 3 to 6 carbon atoms or phenyl;
- $R_4$ represents a hydrogen atom or an alkyl containing 1 to 6 carbon atoms, alkenyl containing 3 to 6 carbon atoms or alkynyl group containing 3 to 6 carbon atoms optionally substituted by a phenyl group or cycloalkyl group containing 3 to 6 carbon atoms;
- $R_5$ represents an alkyl containing 1 to 6 carbon atoms, alkenyl containing 3 to 6 carbon atoms or alkynyl group containing 3 to 6 carbon atoms optionally substituted by a phenyl or cycloalkyl group containing 3 to 6 carbon atoms;
- or $R_4$ and $R_5$ together with the nitrogen atom to which they are attached form a saturated four to seven membered ring in which said nitrogen atom is the only heteroatom in said ring; and its physiologically acceptable salts.

12. A compound of the formula (I)a:

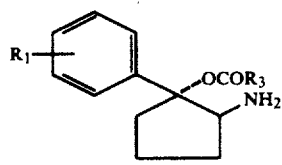

(I)a in which $R_1$ represents a hydrogen atom, a halogen atom or a group $OR_2$ in which $R_2$ represents a hydrogen atom, an alkyl group containing 1 to 6 carbon atoms, an alkanoyl group containing 1 to 6 carbon atoms, an alkenoyl group containing 3 to 6 carbon atoms or a benzoyl group and $R_3$ represents an alkyl group containing 1 to 6 carbon atoms with the proviso that $R_3$ cannot be methyl when $R_1$ is a hydrogen atom; and its physiologically acceptable salts.

13. An analgesic composition comprising at least one compound according to claims 1, 2, 7, 8, 9, 10, 11 or 12 in an amount effective to relieve pain, together with one or more pharmaceutically acceptable carriers or excipients.

14. A process for the preparation of a compound as defined in claim 1 which comprises the step:
(A)(i) in order to prepare a compound as defined in claim 1 wherein $R_4$ and $R_5$ are other than hydrogen atoms, acylating a corresponding alcohol of formula (II):

wherein $R_1$, $R_4$ and $R_5$ are as defined in claim 1 except that $R_4$ and $R_5$ do not represent hydrogen atoms; or
(A)(ii) in order to prepare a compound as defined in claim 1 which is a β-isomer, reacting an aziridine of formula (VIII):

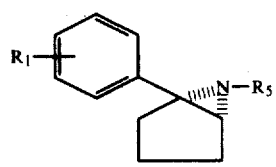

(VIII)

wherein $R_1$ and $R_5$ are as defined in claim 1 with an organic acid of formula:

$R_3COOH$ wherein $R_3$ is as defined in claim 1; or
(A)(iii) in order to prepare a compound as defined in claim 1 wherein $R_4$ is a hydrogen atom and $R_5$ is other than a hydrogen atom or wherein $R_4$ and $R_5$ are the same and are other than hydrogen atoms, subjecting a primary amine of formula (XVIII):

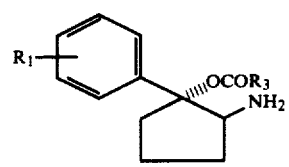

(XVIII)

wherein $R_1$ represents a hydrogen atom, a halogen atom or a group $OR_2$ (wherein $R_2$ is as defined in claim 1) and $R_3$ represents a hydrogen atom or an alkyl group containing 1 to 6 carbon atoms, an alkenyl group containing 3 to 6 carbon atoms or a phenyl group to mono- or di-alkylation by reaction with a compound of formula:

$R_5X$ wherein $R_5$ is as defined in claim 1 and is other than a hydrogen atom and X is a leaving group or by reaction with an appropriate aldehyde or ketone in the presence of hydrogen and a noble metal catalyst; or
(A)(iv) in order to prepare a compound as defined in claim 1 wherein $R_4$ and $R_5$ are both other than hydrogen atoms, reacting a secondary amine of formula (XXII):

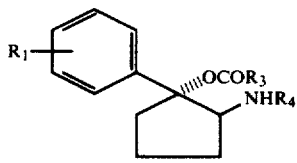
(XXII)

wherein $R_1$, $R_3$ and $R_4$ are as defined in claim 1 and $R_4$ is other than a hydrogen atom with an appropriate aldehyde or ketone in the presence of hydrogen and a noble metal catalyst; and (B) recovering the resulting compound of formula (I) optionally in the form of a physiologically acceptable salt thereof.

15. A process according to claim 14 wherein in step (A)(i) the alcohol of formula (II) is acylated with a formate ester, an acid halide or an acid anhydride.

16. A process according to claim 15, wherein the alcohol is acylated with an acid halide or anhydride at an elevated temperature in the presence of an organic or inorganic base.

17. A process according to claim 14 wherein, in step (A)(ii) the aziridine is reacted with the organic acid at an elevated temperature and in the presence of a solvent.

18. A process according to claim 14 wherein, in step (A)(iii) in order to prepare the compound wherein $R_4$ and $R_5$ are the same and other than hydrogen atoms the primary amine is reacted with an excess of the compound of formula $R_5X$ or with an excess of the aldehyde or ketone in the presence of hydrogen and a metal catalyst.

19. A method for the treatment of a patient suffering from pain which comprises administering to the patient an analgesically effective amount of a compound of formula (I) as defined in claim 1.

* * * * *